(12) United States Patent
Haueter et al.

(10) Patent No.: US 9,050,409 B2
(45) Date of Patent: Jun. 9, 2015

(54) PATIENT DEVICE WITH SEPARATE USER INTERFACE

(75) Inventors: Ulrich Haueter, Grosshöchstetten (CH); Maurice Ducret, Ostermundigen (CH); David Bosshard, Wengi (CH); Thomas Rufer, Ostermundigen (CH); Ivan Heutschi, Grosshöchstetten (CH); Hans-Peter Stoller, Bern (CH); Joël Jeckelmann, Villars-sur-Glâne (CH); Martin Brügger, Köniz (CH); Heiner Kaufmann, Bern (CH)

(73) Assignee: Roche Diagnostics International AG, Rotkreuz (CH)

( * ) Notice: Subject to any disclaimer, the term of this patent is extended or adjusted under 35 U.S.C. 154(b) by 1144 days.

(21) Appl. No.: 11/608,929

(22) Filed: Dec. 11, 2006

(65) Prior Publication Data
US 2007/0165020 A1   Jul. 19, 2007

(30) Foreign Application Priority Data
Dec. 12, 2005  (EP) ..................................... 05027064

(51) Int. Cl.
| G09G 5/00 | (2006.01) |
| G06T 1/00 | (2006.01) |
| A61M 5/142 | (2006.01) |
| G06F 1/16 | (2006.01) |
| A61B 5/00 | (2006.01) |

(52) U.S. Cl.
CPC .......... *A61M 5/14244* (2013.01); *A61B 5/4839* (2013.01); *A61B 5/742* (2013.01); *A61B 5/7445* (2013.01); *A61B 5/7475* (2013.01); *A61M 2205/502* (2013.01); *A61M 2205/505* (2013.01); *G06F 1/163* (2013.01)

(58) Field of Classification Search
CPC ....... A61B 5/0002; A61B 5/74; A61B 5/7445
USPC ...................... 600/300; 340/539.12
See application file for complete search history.

(56) References Cited

U.S. PATENT DOCUMENTS

| 5,847,690 A | * | 12/1998 | Boie et al. ...................... 345/104 |
| 6,371,616 B1 | | 4/2002 | Doany et al. |
| 6,386,706 B1 | * | 5/2002 | McClure et al. .............. 351/237 |

(Continued)

FOREIGN PATENT DOCUMENTS

| JP | 2000-020200 | 1/2000 |
| JP | 2001222067 A | 8/2001 |

(Continued)

*Primary Examiner* — William Thomson
*Assistant Examiner* — Marie Archer
(74) *Attorney, Agent, or Firm* — Dinsmore & Shohl LLP

(57) ABSTRACT

A patient device includes a case and a user interface for interaction between a patient and the patient device. The case may include a projection unit which projects information onto a surface separate from the case. The user interface may include a display unit for displaying information relating to the patient device integrated into the case and an additional display unit for displaying information relating to the patient device, which is external to the case. The externally provided display unit may be coupled to the case such that it can be at least one of folded, tilted, pulled out or unrolled relative to the case.

7 Claims, 2 Drawing Sheets

(56) References Cited

U.S. PATENT DOCUMENTS

| | | |
|---|---|---|
| 6,414,728 B1 * | 7/2002 | Faris et al. .................. 349/10 |
| 6,561,978 B1 | 5/2003 | Conn et al. |
| 6,562,001 B2 | 5/2003 | Lebel et al. |
| 6,643,124 B1 * | 11/2003 | Wilk .................. 361/679.04 |
| 6,740,059 B2 | 5/2004 | Flaherty |
| 6,780,156 B2 | 8/2004 | Haueter et al. |
| 6,790,178 B1 * | 9/2004 | Mault et al. .................. 600/300 |
| 7,343,026 B2 | 3/2008 | Niwa et al. |
| 7,639,209 B2 * | 12/2009 | Sprague et al. .................. 345/8 |
| 2001/0025189 A1 | 9/2001 | Haueter et al. |
| 2002/0023654 A1 * | 2/2002 | Webb .................. 128/899 |
| 2002/0063855 A1 | 5/2002 | Williams |
| 2002/0075240 A1 | 6/2002 | Lieberman et al. |
| 2002/0177781 A1 | 11/2002 | Amano |
| 2003/0144581 A1 | 7/2003 | Conn et al. |
| 2003/0160735 A1 | 8/2003 | Lee et al. |
| 2003/0184575 A1 | 10/2003 | Reho et al. |
| 2004/0070563 A1 | 4/2004 | Robinson |
| 2004/0260233 A1 | 12/2004 | Garibotto et al. |
| 2006/0178600 A1 | 8/2006 | Kennedy et al. |
| 2006/0209020 A1 * | 9/2006 | Scheiblhuber .................. 345/156 |
| 2007/0023044 A1 * | 2/2007 | Kwok et al. .................. 128/204.23 |

FOREIGN PATENT DOCUMENTS

| | | |
|---|---|---|
| JP | 2002524735 | 8/2002 |
| JP | 2002536103 | 10/2002 |
| JP | 2003-004730 | 8/2003 |
| JP | 2004521667 | 7/2004 |
| JP | 2004258714 A | 9/2004 |
| JP | 2007-275217 | 4/2006 |
| WO | 96/36036 | 11/1996 |
| WO | WO 01/65810 A1 | 9/2001 |

* cited by examiner

PATIENT DEVICE WITH SEPARATE USER INTERFACE

CROSS-REFERENCE TO RELATED APPLICATION

This application claims priority to European Patent Application No. 05 027 064.4, filed on Dec. 12, 2005, the content of which is incorporated in its entirety herein.

BACKGROUND

The present invention relates to devices for delivering, testing, administering, injecting or infusing substances, and to methods of making and using such devices. More particularly, it relates to medical devices for delivering, testing, administering, injecting or infusing substances, and to methods of making and such devices. More particularly, the present invention relates to a portable patient device, and to making, using and operating the patient device.

Portable patient devices are known for a multiplicity of applications, uses or treatments, for example to measure physiological parameters and supply medication. These patient devices are now an important aid in and part of diagnosis and therapy. Generally, they allow patients to go about their everyday life without great or burdensome restrictions, while offering doctors, other care-givers, monitors and/or the patients themselves informative measurements under everyday conditions.

An example of a patient device for measuring a physiological parameter is a blood sugar meter, for example the Accu-Chek® blood sugar measurement system from Roche Diagnostics GmbH, Germany. The blood sugar meter analyzes the patient's blood applied on a measurement strip and displays the measured blood sugar value, also known as a glucose value, on a display. A user interface for the interaction between patient and device allows the patient to call up stored measurement values and represent them on the display.

An example of a patient device for supplying medication is an insulin pump, for example the Accu-Chek® insulin pump from Roche Diagnostics GmbH, Germany. A patient carries the insulin pump generally on their body. Via a thin tube whose cannula is placed under the skin, the insulin pump delivers insulin continuously to the body. Microprocessors control a motor which, for example, moves a plunger in an insulin vial via a threaded rod every three minutes. This movement, which corresponds to the respectively programmed basal rate, i.e. the patient's basic insulin demand, supplies the body with the required amount of insulin. The patient can adjust and operate the insulin pump via a user interface, including a display unit (display) and buttons, for example as a function of a blood sugar value measured previously.

A diabetic patient typically always has a blood sugar meter within reachable proximity, for example packaged as a set together with measurement strips. To be able to carry this set with one relatively conveniently and discreetly, the patient device should be as small as possible. This also applies for the insulin pump, which patients would like to carry on the body as conveniently and discreetly as possible. The more a patient device is miniaturized, the smaller the user interface generally becomes. This, however, can reduce its user-friendliness.

SUMMARY

An object of the present invention is to provide a patient device which exhibits a high level of user-friendliness despite having relatively small dimensions.

In one embodiment, the present invention comprises a first device and a peripheral device operably coupled to the main device. The peripheral device may comprise hardware, an interactive display or a combination of both. Both or either of the first and peripheral devices may comprise suitable processing and communication features, and both or either may be at least one of therapeutic and diagnostic.

In one embodiment, the present invention comprises a system comprising a device which is at least one of therapeutic and diagnostic, the device comprising a housing and a user interface, wherein at least a part of the user interface comprises an instrument separable from the housing. In some embodiments, the present invention comprises a patient device comprising a case and a user interface for interaction between a patient and the patient device, wherein at least a part of the user interface is separable from the case and is recognizable by the patient.

In some of the exemplary embodiments of a patient device described herein, at least a part of the user interface of the patient device, especially its display unit, can be represented, presented or provided separately from the actual patient device and recognizably by the patient. Since at least a part of the user interface is represented or provided externally, the size of the representation is no longer subject to the size limitations of the case or housing of the patient device. The user interface, and especially the information intended for the patient, can therefore be represented or displayed with a greater size than on a conventional display of a patient device. The user interface may, for example, be presented on an external display, a table or a screen, for example by projection or broadcasting. This may be advantageous for diabetic patients, who often also have restricted eyesight, because they may be able to see the larger representation better.

The patient device may be employed as a so-called virtual retina display ("VDR"). A virtual retina display is an optical system that creates a virtual image that is projected directly onto the retina of the eye (see, for example, U.S. Pat. No. 5,467,104 A or US 2004/0174599 A1, the disclosures of which are incorporated herein by reference). The virtual image corresponds to the separated user interface or the information intended for the patient, respectively.

In one exemplary embodiment, a patient device which comprises a user interface and a case or housing is part of a patient system. In this patient system, at least a part of the user interface can be represented or presented separately from the case and by an instrument (the instrument being spaced or remote from the case or housing). In some embodiments, the entire user interface can be provided remotely from the case. In some embodiments, the instrument may comprise a virtual retina display creating a virtual image that is projected directly onto the retina of the eye of a patient or person.

Depending on the embodiment, the user interface may be fully or partially integrated in or with the patient device. The sometimes inconvenient intervention directly on or involving the patient device is therefore less necessary or unnecessary. The patient device can therefore also be smaller since, depending on the embodiment, only a minimal user interface, for example a smaller display or no display at all, is used or is necessary in the patient device.

DETAILED DESCRIPTION

Without restricting the protective scope of the present application, various ways of embodying the present invention are described herein with reference to devices for treating diabetes, for example an insulin pump or a blood sugar meter. These patient devices, associated treatment methods and/or methods of making and using such devices, however, are only two examples of patient devices which should be as small as possible but still have a high level of user-friendliness. Pumps for other medications or treatment regimes, lactate meters, pulse and blood pressure meters, ECG devices, etc. are further examples of patient devices in which the present invention may be applied.

With regard to fastening, mounting, attaching or connecting the components of the present invention, unless specifically described as otherwise, conventional mechanical fasteners and methods may be used. Other appropriate fastening or attachment methods include adhesives, welding and soldering, the latter particularly with regard to the electrical system(s) or arrangements. For electrical features or components, suitable electrical components and circuitry, wires, chips, boards, microprocessors, inputs, outputs, displays, control components, etc. may be used. Generally, unless otherwise indicated, materials for making the device of the present invention and/or its components may be selected from appropriate materials such as metal, metallic alloys, ceramics, plastics, etc.

Figure 1:
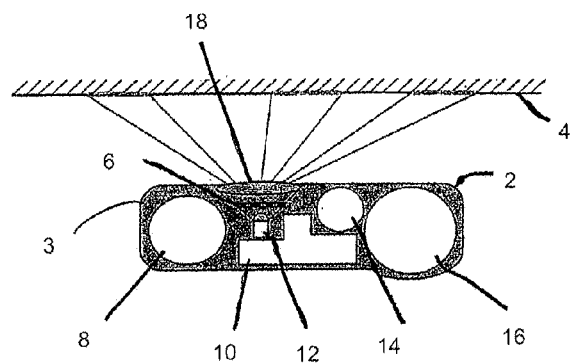
FIG. 1 is a schematic representation of one exemplary embodiment of a patient device comprising a projection instrument.

FIG. 1 is a schematic representation of an exemplary embodiment of a patient device 2, for example an insulin pump. The patient device 2 has a case 3 and a projection instrument, which projects or presents information on a surface 4 remote from the patient device 2. The surface 4 may for example be a table, a wall, a screen, a piece of paper, an article of clothing or the back of a hand. The projected information may, for example, contain the set basal rate. In other exemplary embodiments, the projected information may contain additional information, for example the unit of the basal rate, the date and the time. In general, the term "information" is to be interpreted as any kind of data, symbols, etc. which are relevant to or for the operation of the device and for the patient, irrespective of the way in which they are represented, for example as alphanumeric text, symbols, graphics, image, video or optical, optionally colour-coded signals, etc.

The size of the projected information or any portion thereof may be adapted to the patient's eyesight. The desired size can be adjusted according to requirements and depending on the distance between the patient device 2 and the surface 4. Especially when the patient has restricted or diminished eyesight (for example caused by diabetes) the projected information may be presented with a larger size than on a conventional display integrated in the device. This substantially increases the legibility of the information. For eyesight which is good, the projected information may be presented with a relatively small size so that discreet handling of the patient device 2 is possible.

The projection instrument in the exemplary embodiment shown comprises a projector, which is indicated by a light source 12 for visible light (for example a light-emitting diode (LED), a laser, etc.), an optical lens 18 and an imaging matrix 6 (for example an LCD panel or the like) arranged between the light source 12 and the lens 18. Control electronics 10 are coupled to the projection instrument and generate control signals to drive the imaging matrix 6. In the case of an LCD panel as the imaging matrix 6, the control signals drive individual pixels which thereupon either let pass or block light to project an image on the surface 4.

The functionality of projectors is well known. Relatively small monochrome projectors, for example, are known from their use in electronic alarm clocks which project an image of the time on a wall. In one exemplary embodiment, the patient device 2 may have a projector or the like known from such alarm clock applications or the like. As an alternative to that type of projector, in other exemplary embodiments a miniature beamer developed by the Fraunhofer Institute for Silicon Technology or a Field Lens Design™ projector from Carl Zeiss AG may be used.

In some embodiments, the patient device 2 further comprises a drive instrument 14 (for example a motor or transmission), which acts on an insulin vial 16 and pumps or delivers insulin under the patient's skin from the vial. A voltage source 8, for example a battery, supplies energy for the operation of the patient device 2.

In some embodiments, the projection instrument is part of a user interface of the patient device 2, via which the interaction between patient and device takes place, for example operation or monitoring of the patient device 2 by the patient. The user interface typically comprises input and output instruments, features, structures or devices, for example display units (displays) and operating buttons (e.g., a keyboard, touch screen, etc.). It is therefore to be understood that the patient device 2 has further components (not shown) besides the components mentioned, for example operating buttons or the like by which the patient can operate, control or monitor the patient device 2 and/or operational, therapeutic or diagnostic parameters thereof.

In the exemplary embodiment shown, the patient device 2 does not have a display unit. The information to be represented or presented for the patient or a third party is projected on the surface 4. The case 3 of the patient device 2 can therefore be made with smaller dimensions.

Figure 2:
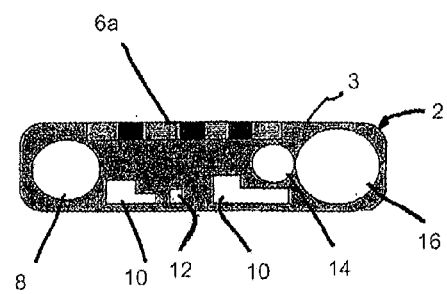
FIGS. 2 and 3 are schematic representations of an exemplary embodiment of a patient device comprising a display and a projection instrument.
Figure 3:
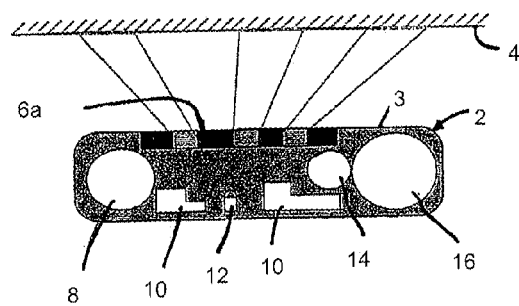

FIGS. 2 and 3 are schematic representations of an exemplary embodiment of a patient device 2 having a display unit 6a, also referred to below as display 6a, and a projection instrument. Similarly to the embodiment shown in FIG. 1, the display 6a may be an LCD panel which is illuminated by the light source 12 for visible light. The control electronics 10 are coupled to the projection instrument and generate control signals for driving the display 6a.

In some embodiments, the display 6a has two functions, i.e. it is used as display unit and as an imaging or projection matrix. The light source 12 is not activated in FIG. 2, so that the display 6a is not illuminated from behind. In this employment and controlled by the control electronics 10, the display 6a presents the information. The patient can therewith read the information directly from the display 6a. In FIG. 3, on the other hand, the light source 12 illuminates the display 6a which acts as imaging matrix, whereby the information is projected on the surface 4. The surface 4 may be a table or one of the surfaces mentioned above.

Figure 4:
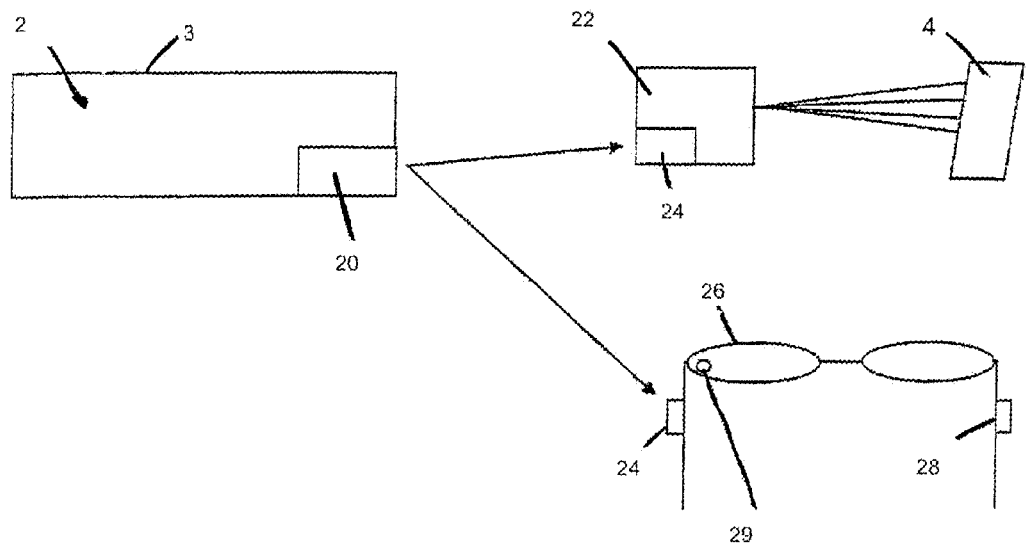
FIG. 4 is a schematic representation of an exemplary embodiment of a patient system comprising a patient device and an external user interface.

FIG. 4 is a schematic representation of an exemplary embodiment of a system having a patient device 2 and an external user interface. Besides the said components such as a drive instrument, an insulin vial and a voltage source, the patient device 2, for example an insulin pump, has a transmitter 20. In the system shown the transmitter 20 can transmit data wirelessly or via cable to a projection instrument 22 or wirelessly to an aid 26 worn by the patient, for example spectacles 26. To this end, the projection instrument 22 and the spectacles 26 respectively have a receiver 24.

In one exemplary embodiment, the transmitter 20 can transmit data wirelessly according to the Bluetooth® standard (serial port profile (SSP)) with an application layer protocol placed above. In other exemplary embodiments, the transmitter 20 may transmit the data according to the IrDA, WLAN (802.11x), Zigbee, WiMax or Mics protocol.

The aid 26, e.g., the spectacles in the depicted embodiment, furthermore has a suitable voltage source 28 and a light source 29, for example a one- or multicoloured light-emitting diode which is fastened to the spectacles 26 so that the patient can see the light emitted by it. Information about the status of the patient device 2 can therefore be communicated to the patient by means of the light source 29, for example a warning message when it is in the stop mode, error or alarm messages, a confirmation after actuating an input button, or a confirmation of the adjusted bolus quantity by repeated optical pulses.

In one exemplary embodiment, the optical pulses replace the acoustic signals conventionally used in patient devices, which under certain circumstances may be perceived as disruptive by the patient or the environment. In another exemplary embodiment, the acoustic signals may be used in addition to the optical pulses. The patient device 2 may in this case suppress the acoustic signals on demand according to patient and environment.

The projection instrument 22 may project the said information about the status of the patient device 2 onto the surface 4. Further information may also be projected onto the surface 4 in the form of any suitable text, symbols, graphics, image, video, etc.

In another exemplary embodiment, the projection instruments described with reference to FIGS. 1-4 may be configured so that they present, represent or provide a virtual keyboard on the surface 4. An instrument for representing a virtual keyboard is commercially available from VKB Inc., USA. The instrument consists of a projection module (having a red laser diode and optics for the projection), an illumination module (infrared laser diode with optics) and a detection module (infrared camera and evaluation electronics). When a letter is typed on the projected keyboard, the finger reflects infrared light which the camera detects. The evaluation electronics determine the letters therefrom and transmit them onto the display.

The preceding instrument, or other suitable instrument, may be integrated as a projection instrument into the patient device 2, as indicated by way of example in FIG. 1. The instrument may alternatively be coupled as a projection instrument to the patient device 2, as indicated by way of example in FIG. 4. The coupling may take place by a wireless communication, cabled transmission link or other suitable communication method.

It is to be understood that the projection instruments may be configured so that they can project not only the information to be represented onto the surface 1, but also the virtual keyboard. The virtual keyboard allows the patient to enter therapy data rapidly and simply. The patient can then conveniently check the entered data on the projected representation.

Figure 5:
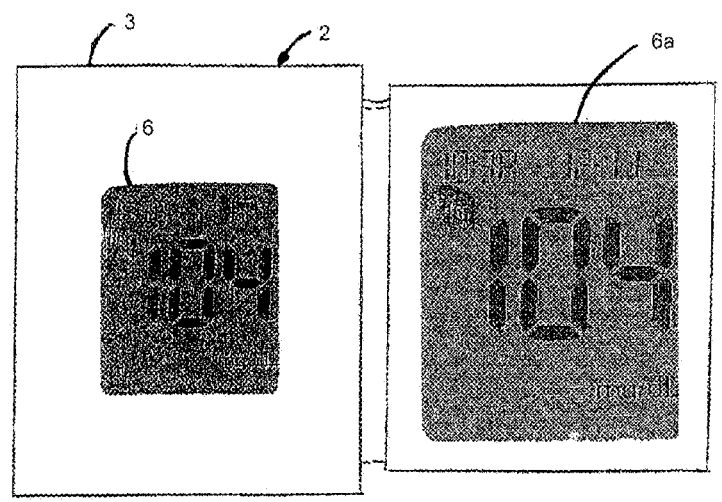
FIG. 5 is a schematic representation of an exemplary embodiment of a patient device comprising an enlarged user interface.

FIG. 5 is a schematic representation of an exemplary embodiment of a patient device 2 having an external and enlarged user interface. The patient device 2 in the exemplary embodiment shown has a display 6 and an external display 6a, which is operably coupled to the patient device 2. As represented in FIG. 5, the external display 6a is larger than the display 6. The information to be represented can, therefore, be presented with or in a larger size and thus more legibly on the external display 6a. In a further exemplary embodiment, no display 6 is provided in or on the patient device 2, but only by the external display 6a.

The external display 6a may be a conventional LCD display, which is fastened on the patient device 2 in such a way that it can be folded or tilted. To this end, the display 6a may be fastened on the patient device 2 by means of an articulation or hinge. The electrical connection of the external display 6a also takes place via the articulation or hinge. Such articulations or hinges are used, for example, in foldable mobile telephones or laptop computers.

In other exemplary embodiment the patient device 2 may have a shaft, from which the external display 6a can be pulled out when needed. A flexible ribbon cable or sliding contacts may be used for the electrical connection of the external display 6a. In some embodiments, the external display 6a, which also may be referred to as a remote display, may be disconnected from and reconnected to the patient device 2.

As an alternative to a rigid LCD display, it is possible to use a flexible display which can be rolled out when needed. The flexible display may be constructed from organic light-emitting diodes (OLED). Such a display has been developed, for example, by the Fraunhofer Institute for Applied Polymer Research.

The exemplary embodiments make it possible to represent or present information on a larger display 6a. Depending on the embodiment, the display 6a may have virtually the size of the patient device 2. This makes the information more legible, especially for patients with restricted eyesight. The display 6a can furthermore facilitate saving space, being able to be put away (e.g., folded, collapsed, etc.) when it is not in use.

The exemplary embodiments of a patient device or patient system as described herein make it possible that at least a part of the user interface of the patient device 2 is represented or presented separately from the case 3. In the exemplary embodiments, the display unit may be omitted, depending on the desired application. The patient device 2 can thus be made as small as practical, without thereby compromising user-friendliness.

Embodiments of the present invention, including preferred embodiments, have been presented for the purpose of illustration and description. They are not intended to be exhaustive or to limit the invention to the precise forms and steps disclosed. Obvious modifications or variations are possible in light of the above teachings. The embodiments were chosen and described to provide the best illustration of the principles of the invention and the practical application thereof, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

The invention claimed is:

1. A patient system comprising a patient device which comprises a user interface and a case, wherein the user interface comprises a first display unit which displays information relating to the patient device and is integrated into the case and a second display unit which displays information relating to the patient device and is external to the case, wherein the second display unit is coupled to the case such that it can be at least one of folded, tilted, pulled out or unrolled relative to the case, wherein the case further comprises a projection unit comprising an optical lens and a light source which provides visible light, and wherein the first display unit is arranged directly between the optical lens and the light source such that the information can be projected onto a surface separate from the case.

2. The patient system according to claim 1, wherein the projection unit comprises a virtual keyboard on the surface, the keyboard providing for the input of data by the patient.

3. The patient system of claim 1, wherein the second display unit is larger than the first display unit.

4. The patient system of claim 1, wherein the second display unit is substantially the size of the case.

5. The system of claim 1, wherein the patient device is an insulin pump.

6. The system of claim 1, wherein the patient device is a blood glucose meter.

7. The system of claim 1, wherein the patient device further comprises a hinge, wherein the hinge couples the second display unit to the case such that it can be at least one of folded, tilted, pulled out or unrolled relative to the case.

\* \* \* \* \*